United States Patent
Tamaoki et al.

[11] Patent Number: 5,843,955
[45] Date of Patent: Dec. 1, 1998

[54] COMPOUND LK6-A

[75] Inventors: Tatsuya Tamaoki; Hiroyuki Nagata, both of Machida; Isami Takahashi, Tama; Mayumi Yoshida, Sagamihara; Yumiko Aotani; Katsuhiko Ando, both of Machida; Keiko Ochiai, Ebina, all of Japan

[73] Assignee: Kyowa Hakko Kogyo Co., Ltd., Tokyo, Japan

[21] Appl. No.: 723,149

[22] Filed: Sep. 30, 1996

[30] Foreign Application Priority Data

Sep. 28, 1995 [JP] Japan .................................. 7-250276

[51] Int. Cl.$^6$ ..................... A61K 31/475; C07D 471/16
[52] U.S. Cl. .............................. 514/292; 546/84
[58] Field of Search .................... 546/84; 514/292

[56] References Cited

U.S. PATENT DOCUMENTS

| | | | |
|---|---|---|---|
| 4,959,370 | 9/1990 | Crews | 514/280 |
| 5,028,613 | 7/1991 | Sun | 514/292 |

OTHER PUBLICATIONS

J. Org. Chem., vol. 59, No. 16 (1994) 4571–4575.
Nature, vol. 280 (Jul. 12, 1979) 148–151.
Imm. Today, vol. 10, No. 1 (1989) 6–9.
Transp. Proc., vol. XI, No. 1 (Mar., 1979) 865–870.
New England J. Med., vol. 268, No 24 (Jun. 13, 1963) 1315–23.
Transp. Proc.s, vol. 22, No. 4 (Aug. 1990) 1606–1612.
Tetrahedron Letters, vol. 31, No. 23 (1990) 3271–3274.
J. Am. Chem. Soc., vol. 112, No. 1 (Jan. 3, 1990) 1–4.

*Primary Examiner*—C. Warren Ivy
*Assistant Examiner*—Evelyn Huang
*Attorney, Agent, or Firm*—Fitzpatrick, Cella, Harper & Scinto

[57] ABSTRACT

The present invention relates to compound LK6-A represented by the formula:

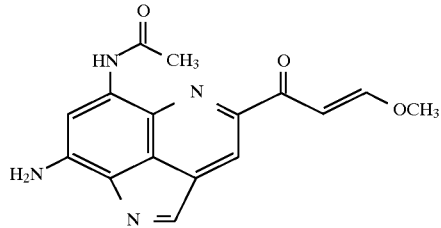

which has immunosuppressive activity, and pharmaceutically acceptable salts thereof.

2 Claims, 1 Drawing Sheet

COMPOUND LK6-A

BACKGROUND OF THE INVENTION

The present invention relates to Compound LK6-A which has immunosuppressive activity.

Examples of low molecular weight immunosuppressive agents so far known are: cyclosporin A [Nature, 280, 148 (1978)]; FK506 [Immunol. Today, 10, 6 (1989)]; mizoribine [Transplantation Proceed., 11, 865 (1979)]; azathioprine [New Eng. J. Med., 268, 1315 (1963)]; and 15-deoxyspergualin [Transplantation Proceed., 22, 1606 (1990)]. These compounds are used for the treatment of autoimmune diseases, allergic diseases, disorders caused by organ transplantation, and so on, but they are not always satisfactory as the therapeutic agents in respect of effectiveness and side effects.

As the compound having a skeleton related to the present compound, plakinidine A, plakinidine B and plakinidine C are also known, and their cytotoxic activity against the L1210 cell has been reported [Tetrahedron Letters, 31, 3271 (1990)]. The activity of plakinidine A and plakinidine B against a parasite *Nippostrongylus brasiliensis* and the reverse transcriptase inhibitory activity of plakinidine A have been reported [U.S. Pat. No. 4,959,370; J. Am. Chem. Soc., 112, 1 (1990)]. However, there has been no report on their immunosuppressive activity.

An object of the present invention is to provide a compound which has potent immunosuppressive activity.

SUMMARY OF THE INVENTION

It has been found that a compound having immunosuppressive activity is produced in the culture of a microorganism. After isolation and purification, its physicochemical properties were studied, whereby it has been found to be a novel compound. The compound has been named LK6-A.

The present invention provides compound LK6-A having immunosuppressive activity which is represented by the formula:

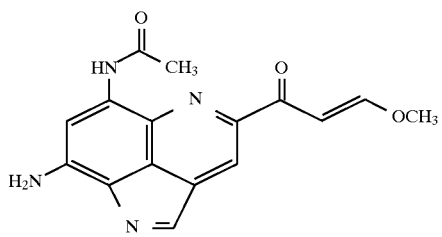

and a pharmaceutically acceptable salt thereof. The compound can be obtained by culturing a microorganism belonging to the genus Streptomyces.

The pharmaceutically acceptable salt of LK6-A includes an inorganic acid addition salt such as hydrochloride, sulfate and phosphate, and an organic acid addition salt such as acetate, maleate, fumarate, succinate, tartrate, citrate, oxalate and methanesulfonate.

BRIEF DESCRIPTION OF THE INVENTION

FIG. 1 is a graph which illustrates the growth inhibitory activity of LK6-A against T cells.

DETAILED DESCRIPTION OF THE INVENTION

Figure 1:
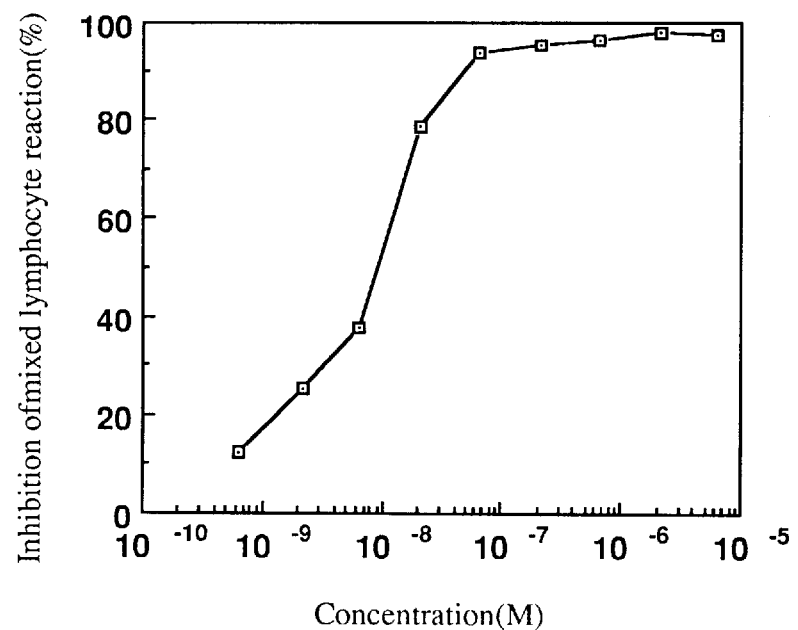

The physicochemical properties of LK6-A are shown below.

The data were obtained by using the following instruments.

Mass spectrum: JEOL LTD., JMS-HX/HX110A Mass spectrometer

UV absorption spectrum: Shimadzu Corporation, UV-2200 Spectrophotometer

IR absorption spectrum: JEOL LTD., JIR-RFX3001 Infrared spectrophotometer

NMR spectrum: JEOL LTD., α400 Nuclear magnetic resonance Bruker, AM500 Nuclear magnetic resonance resonance Bruker, AM500 Nuclear magnetic resonance Melting point: Yanagimoto, Micro melting point apparatus Optical rotation: Nippon Bunko Kogyo Co., Ltd., DIP-370 Digital polarimeter Physicochemical properties of LK6-A Color and form of the substance:
  Reddish orange powder
Melting point (° C.) 275–277
Molecular weight:
  310
Molecular formula:
  $C_{16}H_{14}N_4O_3$
Specific rotation:
  Unmeasurable owing to coloration
Mass spectrum:
  Positive ion FAB-MS m/z; 311.1137 $[M+H]_+$
  (calculated for $C_{16}H_{15}N_4O_3$; 311.1144)
UV absorption spectrum:
  $\lambda_{max}$ nm($\epsilon$) ($CH_3CN$); 467 (8,200), 412 (6,000), 344 (11,900), 284 (16,000), 256 (19,300), 218 (15,200)
IR absorption spectrum:
  $\nu_{max}$ cm$_{-1}$ (KBr); 3367, 1671, 1659, 1633, 1595, 1506, 1362, 1350, 1236, 1128, 1076
$^1$H-NMR spectrum (DMSO-d$_6$):
  δ ppm (integration, multiplicity); 10.136 (1H, s), 8.623 (1H, s), 8.393 (1H, s), 8.211 (2H, br.), 8.143 (1H, s), 7.873 (1H, d, J=12.5 Hz), 7.638 (1H, d, J=12.5 Hz), 3.945 (3H, s), 2.350 (3H, s)
$^{13}$C-NMR spectrum (DMSO-d$_6$):
  124.9 (s), 124.4 (s), 117.6 (d), 110.8 (d), 101.9 (d), 58.5 (q), 24.5 (q)
Solubility:
  Soluble in dimethylsulfoxide (DMSO); sparingly soluble in chloroform, methanol and water; insoluble in hexane.
Thin layer chromatography:
  Rf value; 0.31
  Thin layer; silica gel thin layer (Kieselgel 60F$_{254}$ Art.5719, Merck & Co., Inc.)
  Developing solvent; toluene:ethyl acetate:methanol (5:10:1 v/v/v)

The biological activity of LK6-A is described below by Test Example.

Test Example

Growth inhibition against T cells in murine mixed lymphocyte reaction

Lymph node was aseptically excised from a B10.BR mouse (Japan SLC Inc.) with a solution comprising Hanks' equilibrated salt solution (HBSS, Gibco) and 2.5% fetal calf serum (FCS, Gibco) (hereinafter referred to as HBSS-FCS) and resuspended into a culture medium (RPMI 1640, Nissui) containing 10% fetal calf serum (FCS, Gibco), 1% 200 mM L-Gultamine (Gibco), 1% Penicillin-Streptoymycin liquid (Gibco), 5% NCTC-109 (Gibco), 1% 1M HEPES (Gibco), 7.5% $NaHCO_3$ (SIGMA) and 0.1% 50 mM 2-mercaptoethanol (Nakarai) (hereinafter referred to as RPMI 1640-FCS) to prepared a single cell suspension to give a density of $3 \times 10^6$ cells/ml.

Separately, spleen was aseptically excised from an AKR mouse (Japan SLC Inc.) to prepare a single cell suspension with HBSS-FCS. Then to the cell suspension was added mitomycin C (MMC) (Kyowa Hakko Kogyo Co., Ltd.) to a final concentration of 50 µg/ml, followed by incubation at 37° C. for 30 minutes. Then, the resultant suspension was washed three times with HBSS-FCS and resuspended into a culture medium (RPMI 1640-FCS) to give a density of $1 \times 10^7$ cells/ml.

A mixture of 50 µl of the B10.BR murine lymph node cell suspension prepared as above (containing $1.5 \times 10^5$ cells) and 50 µl of the AKR murine spleen cell suspension prepared as above (containing $5 \times 10^5$ cells) (hereinafter referred to as mixed cell suspension) was put into each well of a 96-well microtiter plate. LK6-A solution was prepared at graded concentrations (final concentration: $7 \times 10^{-10}$ cells to $7 \times 10^{-6}$M). 100 µl of LK6-A solution was put into each well containing the mixed cell suspension, followed by incubation in a 5% $CO_2$-incubator at 37° C. for 72 hours.

Separately, 100 µl of a culture medium (RPMI 1640-FCS) was put into each well containing the mixed cell suspension as a positive control, followed by incubation in a 5% $CO_2$-incubation at 37° C. for 72 hours. Furthermore as a negative control, 150 µl of a culture medium (RPMI 1640-FCS) was put into each well containing 50 µl of the B10.BR murine lymph node cell suspension or 50 µl of the AKR murine spleen cell suspension, followed by incubation in a 5% $CO_2$-incubator at 37° C. for 72 hours.

[$^3$H]Thymidine was added to the wells in an amount of 1.0 µCi/well 18 hours before the end of each incubation. After the completion of incubation, the cells were collected on filter paper with a cell harvester, followed by drying. A toluene scintillator was added to the cells, and the amount of [$^3$H]Thymidine radioactivity incorporated into the cells was determined using a liquid scintillation counter. The T cell growth inhibition rate was calculated according to the following equation.

T cell growth inhibition rate $(\%) = (C-T)/\{C-(A+B)\} \times 100$

C: Amount of [$^3$H]Thymidine radioactivity incorporated into the mixed cell suspension T: Amount of [$^3$H]Thymidine radioactivity incorporated into the LK6-A-treated mixed cell suspension A: Amount of [$^3$H]Thymidine radioactivity incorporated into only the B10.BR murine lymph node cells.

B: Amount of [$^3$H]Thymidine radioactivity incorporated into only the MMC-treated AKR murine spleen cells.

The result is shown in FIG. 1. The 50% inhibitory concentration ($IC_{50}$) of LK6-A against the growth of T cells in murine mixed lymphocyte reaction was $9 \times 10^{-9}$M.

The process for producing LK6-A is described below.

LK6-A can be obtained by culturing in a medium a microorganism belonging to the genus Strentomyces and having the ability to produce LK6-A, allowing LK6-A to accumulate in the culture, and isolating LK6-A from the culture.

As the LK6-A-producing strains of the present invention, any strains which belong to the genus Streptomyces and have the ability to produce LK6-A can be used. In addition, any mutants of such strains which are obtained by various artificial mutation methods such as UV irradiation, X-ray irradiation and treatment with mutagens or by spontaneous mutation may also be used in the present invention, insofar as they have the ability to produce LK6-A. A typical example of a suitable strain is Streptomyces sp. LK6 strain which was newly isolated from soil by the present inventors.

The morphological, cultural, physiological and chemotaxonomic characteristics of Streptomyces sp. LK6 strain are described below.

1. Morphological characteristics
1) Hyphae
   Formation of aerial hyphae: Observed
   Fragmentation and motility of aerial hyphae: Not observed
   Fragmentation and motility of substrate hyphae: Not observed
2) Spores
   Formation and location of spores: Formed on the aerial hyphae
   Formation and location of sporangia: Not observed
   Number of spores in chain formed at the end of the sporophore: 10 or more
   Form of spore chains: Flexuous, spiral, or mass Characteristics of spores:
   Surface; Smooth
   Form and size;
      Short rod ca. 0.5~0.7 µm×0.7~1.0 µm
   Motility of spores and existence of flagella; Not observed
3) Others
   Chlamydospores; Not observed
   Synnemata; Not observed
   Pseudosporangia; Observed
   Branching mode of hyphae; Simple branching 2. Cultural characteristics
   The strain LK6 shows moderate or good growth on synthetic media and natural media which are generally used. The color of the substrate hyphae is white to brown. Formation of soluble brown pigment was observed on some of the culture media.

The cultural characteristics such as growth and color of LK6 strain on various agar media observed after culturing at 28° C. for 14 days are shown below. The color names were given according to the Color Harmony Manual (Container Corporation of America, 4th edition, 1958).

1) Sucrose—nitrate agar medium
   Growth; Poor
   Color of substrate hyphae; White (a)
   Formation and color of aerial hyphae; Poor, Oxford gray (1)
   Soluble pigment; None
2) Glucose—asparagine agar medium
   Growth; Good
   Color of substrate hyphae;
      Rose beige (4ge)—dark brown (5nl)
   Formation and color of aerial hyphae;
      Abundant, white (a)
   Soluble pigment; None
3) Glycerol—asparagine agar medium
   Growth; Good
   Color of substrate hyphae;

Light tan (3gc)—beaver (3li)
Formation and color of aerial hyphae;
   Abundant, white (a)—silver gray (3fe)
Soluble pigment; Formed only a little (ocher)
4) Starch—inorganic salts agar medium
   Growth; Good
   Color of substrate hyphae;
      Light rose beige (4ec)—dark brown (4pn)
   Formation and color of aerial hyphae;
      Abundant, silver gray (3fe)—Oxford gray (1)
   Soluble pigment; Formed (liver brown)
5) Tyrosine agar medium
   Growth; Good
   Color of substrate hyphae;
      Light tan (3gc)—clove brown (3ni)
   Formation and color of aerial hyphae;
      Abundant, white (a)—citron gray (1ge)
   Soluble pigment; None
6) Nutrient agar medium
   Growth; Moderate
   Color of substrate hyphae;
      Camel (3ie)—light brown (3lg)
   Formation and color of aerial hyphae;
      Fair, white (a)
   Soluble pigment; Formed (brown)
7) Yeast—malt agar medium
Growth; Good
   Color of substrate hyphae;
      Camel (3ie)—dark brown (4pn)
   Formation and color of aerial hyphae;
      Abundant, white (a)—gray (f)
   Soluble pigment; Formed (brown)
8) Oatmeal agar medium
   Growth; Moderate
   Color of substrate hyphae;
      Rose beige (4gc)—deep brown (4pl)
   Formation and color of aerial hyphae;
      Fair, white (a)—gray (g)
   Soluble pigment; Formed (liver brown)
3. Physiological characteristics
   The physiological characteristics of LK6 strain are shown below. The result of 1) was obtained after 14 days of culturing and the results of 2)–6) were obtained after 2 to 3 weeks of culturing at 28° C.
   1) Growth temperature range; 10°–40° C.
   2) Liquefaction of gelatin; Negative
   3) Hydrolysis of starch; Positive
   4) Coagulation and peptonization of skim milk powder;
      Negative
   5) Production of melanin-like pigment
      (i) Peptone—yeast—iron agar medium; Positive
      (ii) Tyrosine agar medium; Negative
   6) Assimilability of carbon sources
   As the basis medium, Pridham Gottlieb agar medium was used. In the following, + indicates that the strain utilized the carbon source, − indicates that the strain did not utilize the carbon source, and W indicates that it is not clear whether the strain utilized the carbon source.
      L-Arabinose; −
      D-Xylose; −
      D-Glucose; +
      Sucrose; −
      Raffinose; −
      D-Fructose; W
      Rhamnose; −
      Inositol; −
      D-Mannitol; −
   4. Chemotaxonomic characteristics
   1) Configuration of diaminopimelic acid in whole-cell hydrolyzate; LL-form
   2) Major quinone components of cellular lipid;
      MK-9 (H6), MK-9 (H8)
   The strain is classified in the genus Streptomyces among actinomycetes in view of its characteristics: that spore chains are formed on the aerial hyphae; that it belongs to the Type I cell wall group (LL-diaminopimelic acid, glycine); and that the major quinone components are hexahydrogenated menaquinone 9 [MK-9 (H6)] and octahydrogenated menaquinone 9 [MK-9 (H8)]. The strain was named Streptomyces sp. LK6 and was deposited with the National Institute of Bioscience and Human-Technology, Agency of Industrial Science and Technology with accession number FERM BP-5202.

For the culturing of the LK6-A-producing strains used in the present invention, conventional methods for culturing actinomycetes are generally employed. As the medium, either a synthetic medium or a natural medium may be used insofar as it appropriately contains carbon sources, nitrogen sources and inorganic substances which can be assimilated by the strains employed and the growth- and production-promoting substances required.

As the carbon sources, glucose, starch, dextrin, mannose, fructose, sucrose, lactose, xylose, arabinose, mannitol, molasses, etc. can be used alone or in combination. In addition, hydrocarbons, alcohols, organic acids, etc. may also be used according to the assimilability of the microorganism employed.

As the nitrogen sources, ammonium chloride, ammonium nitrate, ammonium sulfate, sodium nitrate, urea, peptone, meat extract, yeast extract, dry yeast, corn steep liquor, soybean powder, casamino acid, etc. can be used alone or in combination.

If necessary, inorganic salts such as sodium chloride, potassium chloride, magnesium sulfate, calcium carbonate, potassium dihydrogen phosphate, ferrous sulfate, calcium chloride, manganese sulfate, zinc sulfate, and copper sulfate may be added. In addition, trace ingredients that promote the growth of the strain employed and the production of LK6-A may also be added to the medium.

In the culturing, liquid culture, especially submerged stirring culture, is preferably employed. Culturing is carried out at 16° to 37° C., preferably 25° to 32° C., and at pH 4 to 10, preferably 6 to 8. In general, culturing is completed in 1 to 7 days, and LK6-A is produced and accumulated in the culture broth and the microbial cells.

In order to adjust the pH of the medium, aqueous ammonia, ammonium carbonate solution, etc. are used. When the amount of the product in the culture reaches the maximum, the culturing is discontinued.

For the isolation and purification of LK6-A from the culture, an ordinary method for isolating a microbial metabolite from the culture can be utilized.

For example, the culture is filtered to separate a culture filtrate from microbial cells. The microbial cells are extracted with a solvent such as chloroform or acetone. Then, the extract is mixed with the culture filtrate, and the resulting mixture is passed through a column of polystyrene adsorbent such as Diaion HP20 (Mitsubishi Chemical Corporation) to adsorb the active substance, followed by elution with a solvent such as ethyl acetate or acetone. The eluate is concentrated, and the concentrate is applied to silica gel column chromatography, high performance liquid chromatography, and the like to give LK6-A. During the culture and purification steps, LK6-A can be detected by silica gel thin layer chromatography.

In the case where a salt of LK6-A is desired and it is produced in the form of the desired salt, it can be subjected to purification as such. In the case where LK6-A is produced in the free state and its salt is desired, the salt can be formed in the usual way by dissolving or suspending LK6-A in a suitable organic solvent, followed by addition of an acid. LK6-A and pharmaceutically acceptable salts thereof may be in the form of adducts with water or various solvents, which are also within the scope of the present invention.

LK6-A and its pharmaceutically acceptable salts can be used as they are or in various preparation forms for the desired purpose of administration. The pharmaceutical composition of the present invention can be prepared by uniformly mixing an effective amount of LK6-A or its pharmaceutically acceptable salt as an active ingredient with a pharmaceutically acceptable carrier. The carrier may be in any of a wide variety of forms, depending on the most preferable form of preparation for administration. The pharmaceutical compositions are preferably in a unit dosage form suitable for oral administration or parenteral administration.

In the preparation of pharmaceutical compositions for oral administration, any useful pharmaceutically acceptable carriers can be used. For example, liquid preparations for oral administration such as suspension and syrup can be prepared using water; sugars such as sucrose, sorbitol and fructose; glycols such as polyethylene glycol and propylene glycol; oils such as sesame oil, olive oil and soybean oil; antiseptics such as alkyl p-hydroxybenzoate; and flavors such as strawberry flavor and peppermint flavor. Powders, pills, capsules and tablets can be prepared using excipients such as lactose, glucose, sucrose and mannitol; disintegrators such as starch and sodium alginate; lubricants such as magnesium stearate and talc; binders such as polyvinyl alcohol, hydroxypropyl cellulose and gelatin; surfactants such as fatty acid esters; and plasticizers such as glycerin. Tablets and capsules are the most useful oral unit dose forms, since their administration is easy. In the preparation of tablets and capsules, solid pharmaceutical carriers are used.

A solution for injection may be prepared using a carrier such as distilled water, a saline solution, a glucose solution, or a mixture of a saline solution and a glucose solution, if necessary together with a solubilizing agent.

LK6-A and its pharmaceutically acceptable salts may be administered either orally or parenterally by injection. The effective dose and the administration schedule of LK6-A and its pharmaceutically acceptable salts vary depending on the mode of administration, age, weight and conditions of a patient, etc.

Certain embodiments of the invention are illustrated in the following Example.

Example 1

Streptomyces sp. LK6 strain was used as the producer.

The strain was inoculated into 300 ml of a seed medium having the following composition in a 2-l Erlenmeyer flask, and cultured with shaking (rotation: 200 rpm) at 30° C. for 48 hours.

Composition of the seed medium: 30 g/l sucrose, 20 g/l soluble starch, 30 g/l corn steep liquor, 5 g/l dry yeast, and 2 g/l calcium carbonate (pH 7.0 before sterilization)

The resulting seed culture was transferred into 18 l of a fermentation medium having the following composition in a 30-l jar fermentor in an amount of 5% (by volume) of the fermentation medium and the fermentation was carried out at 28° C. with stirring and aeration (rotation: 300 rpm, aeration: 18 l/min.).

Composition of the fermentation medium: 40 g/l soluble starch, 10 g/l soybean powder, 5 g/l corn steep liquor, 5 g/l dry yeast, 0.5 g/l $KH_2PO_4$, 0.5 g/l $Mg_3(PO_4)_2.8H_2O$, 0.01 g/l $ZnSO_4.7H_2O$, 0.001 g/l $CoCl_2.6H_2O$, and 0.001 g/l $NiSO_4$ (pH 7.0 before sterilization, adjusted with NaOH).

Fermentation was carried out for 96 hours without controlling the pH of the medium.

The resulting culture was filtered to separate a culture filtrate from microbial cells. The microbial cells were extracted with acetone, and the extract was concentrated. The concentrate was applied to an adsorption column of HP20 (Mitsubishi Chemical Corporation) and washed with water and 50% methanol, followed by elution with methanol. The eluted fraction was concentrated and extracted with ethyl acetate.

The ethyl acetate layer was concentrated, and the concentrate was applied to a column of silica gel (Lichroprep Si60, Merck & Co., Inc.), followed by development with toluene-ethyl acetate-methanol (10:20:0.45 v/v/v) and fractionation. Then, the eluted active fraction was concentrated, and the concentrate was applied to a column of silica gel (Lichroprep Si60, Merck & Co., Inc.), followed by development with chloroform-methanol (95:5 v/v) and fractionation. The eluted active fraction was concentrated, and the concentrate was subjected to high performance liquid chromatography (HPLC) under the following conditions. Development was carried out with methanol-acetonitrile-10 mM ammonium acetate (1:1:2 v/v/v), and the fraction containing LK6-A (retention time: 40.66 minutes) was obtained. Freeze-drying of this fraction gave 24 mg of LK6-A as reddish orange powder.

HPLC conditions

Column: CAPCELL PAK C18 SG120 (Shiseido Co., Ltd.)

Eluent: methanol-acetonitrile-10 mM ammonium acetate (1:1:2 v/v/v)

Flow rate: 8 ml/min

Detection: 220 nm, 460 nm

Retention time: 40.66 minutes

What is claimed is:

1. Compound LK6-A represented by the formula:

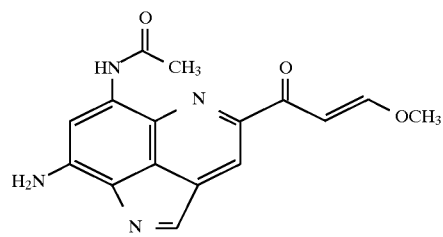

or a pharmaceutically acceptable salt thereof.

2. A pharmaceutical composition comprising a pharmaceutically acceptable carrier and as an active ingredient, an effective amount of the compound as defined by claim 1.

* * * * *